Figure 1:
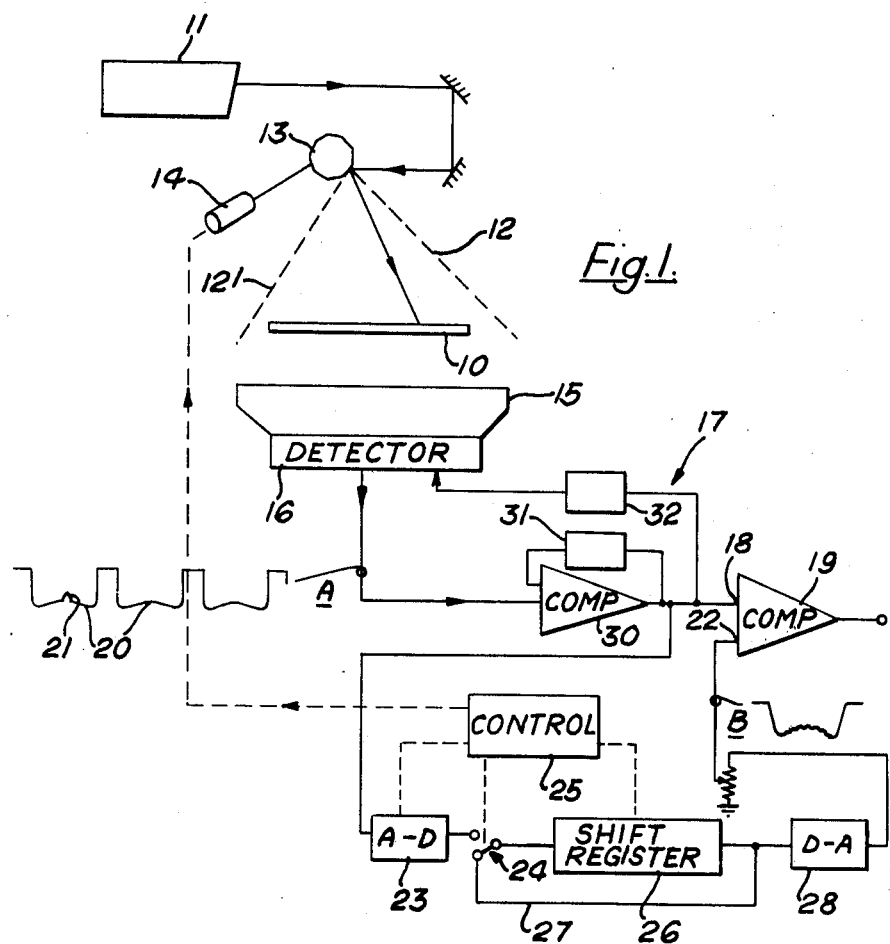

United States Patent [19]

Clarke et al.

[11] 4,155,012
[45] May 15, 1979

[54] DISCRIMINATION CIRCUIT ARRANGEMENTS

[75] Inventors: Graham M. Clarke, Edinburgh; John Bedford, Gorebridge, both of Scotland

[73] Assignee: Ferranti Limited, Hollinwood, England

[21] Appl. No.: 794,511

[22] Filed: May 6, 1977

[30] Foreign Application Priority Data

May 7, 1976 [GB] United Kingdom ............... 18978/76

[51] Int. Cl.² .......................................... G01N 21/32
[52] U.S. Cl. .................................. 250/563; 250/572; 356/431
[58] Field of Search ...................... 250/562, 563, 572; 356/203, 200; 307/358

[56] References Cited

U.S. PATENT DOCUMENTS

| | | | |
|---|---|---|---|
| 3,348,065 | 10/1967 | Schmidt | 307/358 X |
| 3,804,979 | 4/1974 | Knowles | 307/358 X |
| 3,812,373 | 5/1974 | Hosoe et al. | 250/562 |
| 3,843,890 | 10/1974 | Anthony, Jr. et al. | 250/572 X |
| 4,008,405 | 2/1977 | Neumann et al. | 307/358 X |

Primary Examiner—Lawrence J. Dahl
Attorney, Agent, or Firm—Cameron, Kerkam, Sutton, Stowell & Stowell

[57] ABSTRACT

A discrimination circuit operable to discriminate between an input signal in the form of a pedestal and disturbance signals superimposed thereon has an A-D converter to digitize a disturbance-free reference pedestal signal, circulating shift register to store the digitized reference signal, a D-A converter to produce a pedestal signal from the reference signal, a controlling clock to shift the reference signal in the store in synchronism with the incoming signal such that the two pedestal signals are available together, and a comparator to compare the reference signal with the input signal to produce an output caused by differences due to disturbances. The circuit forms part of an optical surface inspection apparatus.

10 Claims, 2 Drawing Figures

DISCRIMINATION CIRCUIT ARRANGEMENTS

This Invention relates to discrimination between signals in the form of pedestals and disturbance signals superimposed thereon.

Such discrimination is particularly applicable to scanning inspection systems of the type in which a beam of optical radiation is caused to scan repetitively across a moving web of material transversely to the direction web motion, radiation reflected from, or transmitted by, the web being collected and applied to a photodetector such that any change in the level of radiation collected due to variations in reflection and/or transmission properties causes a disturbance in an output signal to be produced by the photodetector. Variations in the properties of the web may be due to the presence of faults on or in the material or changes in thickness of the material. If the width of the moving web is less than the scan length then the difference in properties between the web and its transport can produce discontinuities in the photodetector output signal at the edges of the web such that the photodetector signal appears as a series of d.c. voltage pedestal signals having superimposed thereon fault signals in the form of voltage disturbances. The pedestals may be positive-or-negative-going depending on whether the radiation decreases or increases when the beam is off the web. In order to evaluate the fault signals it is necessary to discriminate between the disturbances and the pedestal signals.

Such fault signals may be required to indicate either temporary or permanent changes in the characteristics of the material, either as an absolute change or as a percentage change from a desired norm.

In general such pedestal signals are not "clean", that is they depart from a rectangular profile by non-vertical edges and by height variations throughout the pedestal which variations may be of the same order of magnitude as disturbances superimposed thereon.

A number of methods have been proposed for discriminating between disturbance signals and pedestals. In one method, the subject of co-pending application number 32270/74, the input signal is differentiated to remove the d.c. component of such pedestal but leaving a decaying impulse at the beginning and end thereof as well as high frequency disturbances. The leading edge of the impulse is used to trigger a circuit which produces for each pedestal a replica of the decaying impulse free of any disturbances (by differentiation of a step equal in magnitude to the pedestal) and this replica is compared with the differentiated input signal so that only disturbances present on the input signal are passed to further circuitry. Another method, described in British Pat. Nos. 1,303,041 and 1,303,042 comprises passing each pedestal of the input signal through a filter operating in a high-pass mode while the discontinuities of the leading and trailing edges are processed and in a low-pass mode while the remainder of the pedestal is processed to remove discontinuities; in this way, for each pedestal of the input signal ideally a duplicate pedestal is formed filtered of disturbances and which can be compared with the unfiltered input signal to provide only disturbance signals.

In the first described method, which is based on a.c. operation (whereby d.c. and low frequency components effectively are removed from the signal) problems can be encountered with long duration disturbances which when they are differentiated with the pedestal signal, produce signals which may decay in amplitude in less time than the duration of the disturbance, thereby making the correct sizing of faults which give rise to the disturbances unreliable.

In the second described method which is based on d.c. operation (by the duplication of each pedestal) disturbances of any duration can be measured for size, but difficulty in confining the switch of filter characteristics to the edges of the pedestal may permit disturbances adjacent said edges to be present on the duplicate signal and so eliminated in the comparison.

It is an object of the present invention to provide a discrimination circuit for, and a method of, discriminating between a pedestal signal and disturbance signals superimposed upon the pedestal signal which mitigates some or all of the above disadvantages, and a scanning inspection system incorporating such a circuit.

According to one aspect of the present invention a discrimination circuit comprises input means arranged to receive input signals in the form of pedestals on which disturbances may be superimposed, means operable to store a reference signal derived from a pedestal signal free of disturbances and to apply the reference signal to comparison means in synchronism with signals derived from subsequent input signals, the comparison means producing an output signal indicative of deviation of the input signal from the reference signal.

The means for storing the reference signal may comprise A–D conversion means operable to digitise a reference signal applied to the circuit into a predetermined number of words, a shift register to receive and store each word as it is formed, switching means operative when a reference signal is being digitised to connect the shift register input to the A–D conversion means and operative when input signals are being received by the circuit to connect the shift register input to the shift register output to form a circulating register, D–A conversion means operable to receive each word as it is shifted out of the register to produce from the predetermined number of words an analogue signal corresponding to the reference signal, and control means operable to control shifting in the register in synchronism with each pedestal of the input signal.

The discrimination circuit may include a logarithmic amplifier by way of which the input signals are applied both to the storage means and the comparison means such that the signal produced by the comparison means is indicative of the ratio of the magnitude of input signal to the magnitude of the reference signal.

According to another aspect of the present invention a method of discriminating between a circuit input signal in the form of a pedestal and disturbances superimposed thereon comprises storing digitally a predetermined number of words corresponding to the profile of a pedestal signal free of disturbances, reading the stored words in synchronism with each pedestal of an input signal, converting the stored words into a disturbance-free reference pedestal signal and comparing it with a pedestal derived from the input signal to produce an output signal comprising substantially only deviations from the reference signal due to disturbances on the input signal.

The reference pedestal signal may be stored in the input signals compared therewith in logarithmic form such that the output signal is indicative of the proportional deviation of the input signal from the reference signal.

To accommodate changes in the form of the pedestals of the input signal the whole reference pedestal signal may be replaced periodically, or alternatively, may be renewed progressively by replacing a different part of the reference pedestal signal periodically until after a predetermined number of periods the whole reference signal has been replaced. Said different part may be so small in relation to the whole pedestal signal and any disturbances that a portion of any disturbance appearing in the replacement part does not significantly effect the stored signal.

According to yet another aspect of the present invention a scanning inspection system comprises a source of a beam of optical radiation, scanning means operable to scan the beam repetitively over the surface of a relatively moving object and a detector of radiation reflected from, or transmitted by, the object, and a discrimination circuit as defined in any one of the six preceding paragraphs to which signals representative of the level of detected radiation are applied as reference and input signals.

Figure 2:
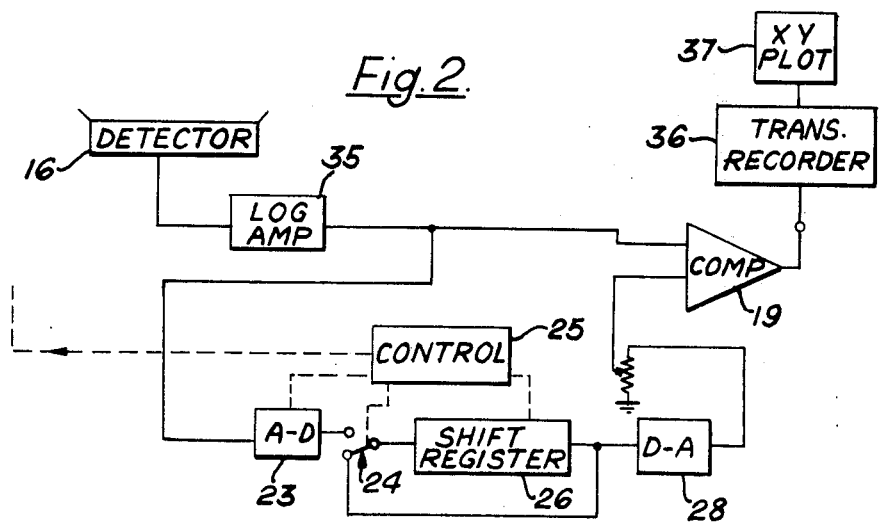

Embodiments of the invention will now be described by way of example with reference to the accompanying drawing, in which:

FIG. 1 is a schematic elevation of a scanning inspection system of the type described operating in a transmission mode and a block diagram of one form of discrimination circuit according to the present invention and the waveforms of signals appearing at points indicated in the circuit, and FIG. 2 is a block diagram of a modified form of discrimination circuit according to the present invention.

Referring to FIG. 1 a web 10 of material, caused to move past the inspection system in a plane extending out of the plane of the Figure, is transmissive of optical radiation emitted in a beam from a laser 11 and which beam is caused to scan across the web transversely to the direction of the web motion between scan limits 12 and 12' by a rotatable multifaceted mirror 13 driven by motor 14.

Optical radiation transmitted by the web is collected by a receiver 15 including a photomultiplier detector 16 which produces a detector signal.

The detector signal (whose waveform at A is shown for three successive scans) is passed by way of an amplitude control arrangement 17 (described hereinafter) and the signal thus derived from the input signal is applied to one input 18 of comparison means 19.

The signal A comprises a succession of voltage pedestals 20 each corresponding in duration to a single scan of the web. In the case of transmission the signal level is at a maximum for direct reception (off the web) but falls for radiation received by way of the web, thus providing negative-going pedestal signals. Any changes in the amount of radiation collected by the photomultiplier throughout the scan and which are characteristic of the transmissivity of the material or of the light collection arrangement manifest themselves as relatively low frequency undulations in the amplitude of each pedestal, and all of the pedestals have substantially the same profile for a particular set of conditions. Changes in the amounts of light collected due to irregular changes in web transmissivity, that is, surface or internal faults, or changes in thickness, appear as relatively high frequency disturbances 21 superimposed on the pedestals.

The discrimination circuit input signal A is fed to the input 18 of the analog comparison means 19 with a reference pedestal signal B free of disturbances but having the characteristic low frequency undulations, fed to a second input 22 of the comparison means.

The reference pedestal signal B is stored in the circuit by introducing thereto a disturbance-free pedestal produced by scanning web material known to be free of defects and feeding detected signals to an A–D converter 23 where it is digitised into L words of M bits. For a homogeneous material this may be achieved by a single scan over part of the web, or by averaging several such scans, so that in the single pedestal signal produced the pedestal is effectively split into L segments by the control means each segment being represented by one of the L words and the amplitude of signal in each segment in turn being represented by the length of the corresponding word.

For an inhomogeneous material storage of a reference pedestal signal is achieved by towing a small, substantially homogeneous, sample of the material along the line of scan. In this case the sample location throughout the path is related to a corresponding one of the L words so that as it is towed and subjected to continuous scanning the signal received in any location is digitised as the magnitude of the number represented by a word in that location and continuously up-dated until the sample enters the next location when the received signal provides the next word. The A–D converter applies each word as it is formed to switching means 24 which under the control of control means 25 transfers the word into a shift register 26 where it is stored. The control means comprises a clock oscillator which is connected to the shift register and the A–D converter to operate both in synchronism. The clock oscillator is also connected by way of a frequency divider to control the scanning speed of the motor 14 to synchronise the scanning with the transfer of digital information. Each of the L words formed from the pedestal are stored serially and are shifted through the register by signals from the control means.

When the L words of the digitised pedestal have been stored the switching means is operated to connect a signal path 27 from the shift register output to the shift register input to form a circulating store and as each word is shifted out of the register it is re-entered so that after L have been shifted said L words occupy the same positions in the register.

Each word as it is read out of the register is applied to a D–A converter 28 which provides a signal of amplitude equivalent to the corresponding part of the reference pedestal fed into the circuit and all L words form an analogue representation of the reference pedestal signal, which signal is shown at B. Thus if the register is triggered in synchronism with each pedestal of the input signal such that the L words are shifted from the register in a time corresponding to the duration of the pedestal then an analogue reference signal is produced free of high frequency disturbances for comparison with the input signal.

In a scanning inspection system employing a repetitively scanned beam it is convenient to drive the motor 13 of the scanning means under the control of the control means 25 such that the surface is scanned and each pedestal of the input signal formed in synchronism with the reproduction of the reference pedestal signal B.

Amplitude match between the currently received and reference pedestal signals is achieved by clamping the received signals with respect to maximum and minimum transmission through the material in the level control arrangement 17, and controlling the amplitude of the received signals with respect to the level of the reference pedestal signal. The level control arrangement 17 comprises an amplifier 30 which receives negative feedback by way of a network 31 to clamp the signal with respect to "black" level, that is, no transmission. The output signal of amplifier 30 is also fed back, by way of a peak level detection circuit 32, to control the gain of the photomultiplier detector 16 to establish the maximum level of the detector signal for material having perfect transmission.

It will be appreciated that the success with which such disturbances can be detected depends on the instantaneous matching between the profiles of the regenerated reference pedestal signal and the pedestal signal of the input signal.

Any analogue signal such as B which is produced from digitally stored information will have discontinuities due to discrete voltage levels making up the signal (shown exaggerated in the Figure) and the instantaneous accuracy of the profile, even if the signal is smoothed, can limit the choice of threshold level introduced by the potentiometer 22. The amplitude of the discontinuities is determined by the number of bits in each word of the digitised signal. In order to reproduce the reference pedestal signal with the maximum resolution a large number of bits are required to each word; but as the words are shifted serially in the register, the speed at which all L words can be read limits either the surface scanning speed (duration of pedestals) or the length of each word.

It has been found in a scanning inspection system having a 200 μs scan time that 8 bit words can be shifted at 1,000 words/scan and provide an analogue reference pedestal signal with approximately 0.25% accuracy of amplitude.

It will be appreciated that in order to maintain the integrity of the comparison measurements changes in the amount of radiation received since the storage of the reference signal should be taken into consideration. Changes due to rapid variations in ambient light received and which would introduce a.c. components to the signal are reduced as far as possible by shielding of the receiver and by introducing a feedforward gain control loop (not shown) into the level control arrangement 17. Changes over a relatively long period of time which cause the profile of the received signal to change, which changes would cause a difference signal to be produced by the comparison means for each scan, are reduced in their effect by updating the stored signal after an appropriate number of scans.

Where the surface being scanned has uniform reflectivity updating the stored information is achieved by operating the switching means during one scan of the surface so that as, for the scan, the previously stored profile information is shifted out of the register and converted into an analogue signal for comparison with the input signal, the pedestal of the input signal is digitised and shifted into the register. Of course in such replacement of the reference pedestal signal it is essential that the pedestal digitised is free of disturbances. This may be ensured by running a piece of flawless material past the scanning station and/or examining the output signal of the comparison means 19 for several scans after the reference signal has been replaced for apparent disturbance signals appearing at the same place in each scan, which apparent disturbances are indicative of a disturbance on the reference pedestal signal. Such detection could be used to indicate replacement of the reference pedestal signal in a subsequent scan. The possibility of storing a faulty reference pedestal may be lessened by examining the output of the comparator for several scans before it is intended to replace the reference pedestal signal to ensure that a fault free area of the surface is under examination.

Alternatively, and particularly where the surface has small reflection non-uniformities, the reference pedestal signal may be renewed progressively by operating the switch to renew each word in turn over a predetermined number of scans until the whole reference pedestal signal is replaced. The signal may be replaced one word per scan for L scans. Using this procedure it is possible to update the stored signal by a small amount each scan such that if the replacement part of the signal contains a portion of a disturbance signal such part is too small to have any significant effect on the whole stored signal.

Where the width of the web is large making it desirable to increase the separation of scanning means and the web the receiver may be located close to the web to maximise the collection of light. The receiver may then comprise a plurality of separate units stacked adjacent each other across the width of the web to receive light transmitted by every part thereof. The profile of the pedestal signal received in each scan is complicated by the effects of junctions between the separate units but as the stored reference pedestal signals results from light reception by the separate units the junction effect will be eliminated in the comparison operation.

In the case particularly of transmission where it is desired to detect changes in thickness of a material then it may be advantageous to detect the changes in relation to a mean value of thickness of a predetermined sample. The transmission thickness characteristics of materials are generally substantially exponential, that is, transmitted radiation falls exponentially with thickness so that a logarithmic relationship between signals produced from transmitted light is linearly related to changes in thickness.

Referring to FIG. 2, the block diagram of the discrimination circuit contains many of the components of the circuit shown in FIG. 1 and such components have like reference numerals.

Signals produced by the photomultiplier detector 16 are fed to the comparison means 19 and (when appropriate) to the A-D converter 23 by way of a logarithmic amplifier 35.

The reference signal is loaded into the storage means by performing a sample scan over a sample portion of web having predetermined properties, that is, a mean value of thickness, or by towing a small sample of the mean value of thickness along the line of scan as detailed for the first described embodiment. It will be appreciated that the gain of the input signals is controlled with respect to unity transmission, that is, no material and to the signal received from the sample so that an output signal of the comparison means 17 represents log (input signal) - log (reference signal) which is equal to log (input signal/reference signal) and proportional to the ratio of thickness of the scanned material to the sample, and the percentage change from the mean value. The output signal of the comparison means may be taken, as shown, by way of a buffer store 36, such as a transient event store, and an x-y plotter 37 although other forms of output such as an alarm or correction signal to a manufacturing process may be produced.

The above assumed exponential relationship between thickness and transmission depends largely on the ability to collect all of the light transmitted. Where this is not possible any departure of the true relationship from exponential can be minimised by providing correction calibrations for departures from the mean value of the sample.

The second described embodiment may also be operated with a "wide" receiver constructed of separate units, signal variations due to junctions between adjacent ones being eliminated by comparison with the stored reference signal.

For high accuracy applications it is desirable to have in each scan a portion of unity transmission, and a permanent sample of material to provide in each scan the mean signal value for the material. A separate sample, producing the same mean signal value is required for towing along the line of scan to form or replace the stored reference signal in order that the time it spends traversing the web position does not permit drift of the circuit from the mean signal value provided by the permanent sample.

It will be appreciated that while the above described embodiments have related specifically to radiation transmitted by the scanned material, the invention may also be performed by receiving radiation reflected from the web.

What we claim is:

1. A discrimination circuit operable to discriminate between signals in the form of pedestals and disturbance signals superimposed thereon comprising input means arranged to receive input signals in the form of pedestals on which disturbances may be superimposed, comparison means having one input connected to the input means, and means operable to store a reference signal derived from a pedestal signal free of disturbances and to apply the stored reference signal to another input of the comparison means in synchronism with signals derived from subsequent input signals.

2. A discrimination circuit as claimed in claim 1 in which the means for storing the reference signal comprises A-D conversion means connected to the input means and operable to digitise a reference signal applied to the circuit into a predetermined number of words, a shift register to receive and store each word as it is formed, switching means operative when a reference signal is being digitised to connect the shift register input to the A-D conversion means and operative when input signals are being received by the circuit to connect the shift register input to the shift register output to form a circulating register, D-A conversion means operable to receive each word as it is shifted out of the register to produce from the predetermined number of words analogue signal corresponding to the stored reference signal, and control means operable to control shifting in the register in synchronism with each pedestal of the input signal.

3. A discrimination circuit as claimed in claim 1 wherein the input means includes a logarithmic amplifier by way of which the input signals are applied both to the storage means and the comparison means such that the signal produced by the comparison means is indicative of the ratio of the magnitude of the input signal to the magnitude of the reference signal.

4. A method of discriminating between an input signal in the form of a pedestal and disturbance signals superimposed thereon comprising storing digitally a predetermined number of words corresponding to the profile of a pedestal signal free of disturbances, reading the stored words in synchronism with each pedestal of an input signal, converting the stored words into a disturbance-free reference pedestal signal and comparing it with a pedestal derived from the input signal to produce an output signal comprising substantially only deviations from the reference signal due to disturbances on the input signal.

5. A method of discriminating as claimed in claim 4 in which the words corresponding to the reference pedestal signal are stored and the input signals compared therewith are in logarithmic form such that the output signal is indicative of the proportional deviation of the input signal from the reference signal.

6. A method of discriminating as claimed in claim 4 in which the predetermined number of words stored are derived from an input signal.

7. A method of discriminating as claimed in claim 6 in which the stored reference pedestal signal is replaced periodically by one derived from an input signal.

8. A method of discriminating as claimed in claim 6 in which the stored reference pedestal signal is replaced progressively by replacing a different stored word derived from each of a succession of input signals.

9. A scanning inspection system comprising a source of a beam of optical radiation, scanning means operable to scan the beam repetitively over the surface of a relatively moving object, a detector of radiation reflected from, or transmitted by, the object, the detector producing signals in the form of pedestals upon which disturbance signals may be superimposed, a discrimination circuit operable to discriminate between the pedestal signals and the disturbance signals, and means for selectively applying to the discrimination circuit either disturbance-free reference pedestal signals or input signals from the detector, the discrimination circuit including input means arranged to receive signals from the detector, comparison means having one input connected to the input means, and means operable to store a reference signal derived from a pedestal signal free of disturbances and to apply the stored reference signal to another input of the comparison means in synchronism with signals derived from subsequent input signals.

10. A method of optically inspecting an object comprising scanning a beam of optical radiation repetitively across the object, detecting light reflected from, or transmitted by, the object to produce electrical signals which have amplitudes related to the intensity of light detected and which are in the form of pedestals upon which disturbance signals may be superimposed, and discriminating between the signal and a reference signal by storing digitally a predetermined number of words corresponding to the profile of a pedestal signal free of disturbances, reading the stored words in synchronism with each pedestal of an input signal, converting the stored words into a disturbance-free reference pedestal signal and comparing it with a pedestal derived from the input signal to produce an output signal comprising substantially only deviations from the reference signal due to disturbances on the input signal.

* * * * *

UNITED STATES PATENT AND TRADEMARK OFFICE
CERTIFICATE OF CORRECTION

PATENT NO. : 4,155,012
DATED : May 15, 1979
INVENTOR(S) : Graham Morley Clarke

It is certified that error appears in the above-identified patent and that said Letters Patent are hereby corrected as shown below:

IN THE ABSTRACT

Line 4, --digitize-- spelled correctly in Patent. "digitise" spelled incorrectly in specification.

Line 5, --digitized-- spelled correctly in Patent. "digitised" spelled incorrectly in specification.

Claim 2, Column 7

Line 44, "digitise" spelled incorrectly, correct spelling --digitize--

Line 48, "digitised" spelled incorrectly, correct spelling --digitized--

Signed and Sealed this

Ninth Day of October 1979

[SEAL]

Attest:

RUTH C. MASON
Attesting Officer

LUTRELLE F. PARKER
Acting Commissioner of Patents and Trademarks